(12) United States Patent
Stine et al.

(10) Patent No.: US 9,456,883 B2
(45) Date of Patent: Oct. 4, 2016

(54) SYSTEMS AND PROCESSES FOR FABRICATING DENTAL RESTORATIONS

(71) Applicant: Jensen Industries Incorporated, North Haven, CT (US)

(72) Inventors: David J. Stine, Cheshire, CT (US); Donald F. Cornell, Madison, CT (US)

(73) Assignee: Jensen Industries Inc., North Haven, CT (US)

( * ) Notice: Subject to any disclaimer, the term of this patent is extended or adjusted under 35 U.S.C. 154(b) by 266 days.

(21) Appl. No.: 14/086,612

(22) Filed: Nov. 21, 2013

(65) Prior Publication Data

US 2014/0140783 A1 May 22, 2014

Related U.S. Application Data

(60) Provisional application No. 61/729,083, filed on Nov. 21, 2012, provisional application No. 61/767,571, filed on Feb. 21, 2013.

(51) Int. Cl.
*A61C 13/00* (2006.01)
*A61C 9/00* (2006.01)

(52) U.S. Cl.
CPC ....... *A61C 13/0004* (2013.01); *A61C 13/0006* (2013.01); *A61C 9/0046* (2013.01); *Y10T 409/30084* (2015.01); *Y10T 409/30112* (2015.01)

(58) Field of Classification Search
USPC .......................................... 700/98, 2; 433/24
See application file for complete search history.

(56) References Cited

U.S. PATENT DOCUMENTS

| | | | | |
|---|---|---|---|---|
| 6,575,751 B1* | 6/2003 | Lehmann | ............. | C07K 14/705 433/223 |
| 6,648,640 B2* | 11/2003 | Rubbert | ................... | A61C 7/00 433/24 |
| 7,387,511 B2* | 6/2008 | Marshall | ................ | A61C 7/146 433/24 |
| 8,521,317 B2 | 8/2013 | Schneider et al. | | |
| 8,738,165 B2* | 5/2014 | Cinader, Jr. et al. | ........... | 433/24 |
| 2005/0003329 A1* | 1/2005 | Lehmann | ............. | C07K 14/705 433/223 |
| 2005/0142517 A1* | 6/2005 | Frysh | ................ | A61C 13/0004 433/173 |
| 2005/0144222 A1* | 6/2005 | Marshall | ............ | A61C 13/0004 709/203 |
| 2008/0261165 A1 | 10/2008 | Steingart et al. | | |
| 2009/0298017 A1* | 12/2009 | Boerjes | ................ | A61B 5/4547 433/214 |
| 2012/0100508 A1* | 4/2012 | Lehmann | ............. | C07K 14/705 433/223 |
| 2012/0231421 A1* | 9/2012 | Boerjes | ................ | A61B 5/4547 433/223 |

* cited by examiner

*Primary Examiner* — Kidest Bahta
(74) *Attorney, Agent, or Firm* — Pepper Hamilton LLP

(57) ABSTRACT

A collaborative approach, incorporating a server for data transmission, security verification, and authentication verification, is implemented between a dental office and a dental laboratory to fabricate a designed dental restoration. A scanner is used in a dental office to take a scan of a patient's mouth. The dental laboratory designs the dental restoration with specialized design software taking into account the scan of the mouth as well as a prescription from the dental office. The parameters defining the designed dental restoration are contained in a design file. The design file is used to create milling specifications defining instructions for milling the designed dental restoration. The materials for the dental restoration are loaded into a mill, where the dental restoration is fabricated in accordance with the milling specifications. Security verification ensures authorized materials are used, and authentication verification ensures authorized materials and processes are used.

19 Claims, 5 Drawing Sheets

SYSTEMS AND PROCESSES FOR FABRICATING DENTAL RESTORATIONS

CROSS REFERENCE TO RELATED APPLICATIONS

This application claims priority to U.S. Provisional Patent Application Nos. 61/729,083 filed Nov. 21, 2012 and 61/767,571 filed Feb. 21, 2013, each of which are incorporated herein by reference in their entirety.

TECHNOLOGY FIELD

The present invention relates generally to fabricating dental restorations, and more particularly to fabricating dental restorations using a collaborative approach between a dental office and a dental laboratory with security and authentication measures to verify the use of authorized materials and/or authorized processes.

BACKGROUND

Traditional methods for fabricating dental restorations involve a dentist providing a dental laboratory with a physical impression of a patient's prepared tooth using impression materials or a digital scan of a patient's prepared tooth generated by a scanner, such as an intra-oral scanner. The fabrication of the dental restoration is then prepared remotely at the dental laboratory, requiring the patient to return to the dental office at a subsequent day to be fitted with the dental restoration upon receipt from the dental laboratory.

Other methods for fabricating dental restorations require a dental office to purchase and maintain all of the equipment necessary for fabricating the dental restoration for a patient, including the scanner, the software for designing the dental restoration, and the mill and the associated software for shaping and preparing the dental restoration. This method requires the purchase and maintenance of expensive equipment, as well as ongoing training of dental office personnel.

This document describes systems and processes for fabricating dental restorations without the need to have multiple visits by a patient and without the costly equipment and training of personnel at a dental office. This document further describes authentication and security aspects for the fabrication of dental restorations to verify the use of authorized materials and/or authorized processes in fabricating the dental restorations.

SUMMARY

Embodiments of the present invention provide a system and a method for fabricating dental restorations in which a hybrid approach between a dental office and a dental laboratory is implemented.

According to aspects of the invention, a server is configured to facilitate communication between a dental office and a dental laboratory. In an embodiment, the communication between the entities includes: a scan file transmitted by the dental office to the dental laboratory, the scan file comprising a scan of a patient, wherein the scan file is generated by a scanner located in the dental office; and design characteristics transmitted by the dental laboratory to the dental office, the design characteristics for a designed dental restoration associated with the scan file, wherein the design characteristics comprise at least one of (i) a design file defining parameters of the designed dental restoration and (ii) milling specifications defining instructions for milling the designed dental restoration. A mill located at the dental office fabricates the designed dental restoration in accordance with the design characteristics. Although much of the disclosure herein is directed to an exemplary centralized server, in other embodiments, the server functionality can reside locally, for example in a local PC and/or with local software.

In one embodiment, the design characteristics received by the dental office comprise the design file defining parameters of the designed dental restoration. A computer-aided manufacturing (CAM) processor at the dental office formulates the milling specifications from the design file and provides the milling specifications to the mill for fabrication of the designed dental restoration. The design file defining parameters of the designed dental restoration is created by a computer-aided design (CAD) processor at the dental laboratory based upon the scan file and a prescription provided by the dental office. The prescription comprises one or more of: (i) a tooth number; (ii) a type of dental restoration; (iii) a restorative material; (iv) a shade for the designed dental restoration and (v) medical data (e.g., patient name, doctor name, date, etc.). Additional information may also be included.

In another embodiment, the design characteristics received by the dental office comprise the milling specifications defining instructions for milling the designed dental restoration, wherein a computer-aided manufacturing (CAM) processor at the dental laboratory formulates the milling specifications from the design file and provides the milling specifications to the mill at the dental office for fabrication of the designed dental restoration. In this embodiment, the design file defining parameters of the designed dental restoration is created by a computer-aided design (CAD) processor at the dental laboratory based upon the scan file and a prescription provided by the dental office.

According to an embodiment, the server is also configured to facilitate authentication between the dental office and the dental laboratory, including verifying the scan file transmitted by the dental office and verifying the design characteristics transmitted by the dental laboratory. Verifying the scan file comprises, according to an embodiment, the server confirming at least one of: (i) authenticity of the scan file; (ii) authenticity of a prescription associated with the scan file; and (iii) a pre-existing relationship between the dental office and the dental laboratory. Verifying the design characteristics comprises, according to an embodiment, the server confirming at least one of: (i) authenticity of the design characteristics; and (ii) a pre-existing relationship between the dental laboratory and the dental office.

According to another embodiment, the server is further configured to verify the fabricated designed dental restoration, comprising: receiving, at the server from the dental office, information associated with the fabricated designed dental restoration; confirming, by the server, that that fabricated designed dental restoration satisfies pre-determined conditions; transmitting, by the server, an authentication of the fabricated designed dental restoration to the dental office; and printing, by an authentication processor at the dental office, an authentication indication associated with the fabricated designed dental restoration.

Other embodiments relate to verifying aspects relating to a dental restoration. According to an embodiment, a method includes: receiving, by a server coupled to a dental office and to a dental laboratory, one or more identifiers from one or more of the dental office and the dental laboratory, the one or more identifiers respectively relating to a frame of material for the dental restoration and a package of a plurality of frames; comparing, by the server, the one or more identifiers to authorized identifiers stored in a database accessible by the server; comparing, by the server, data associated with the one or more identifiers to data contained in a corresponding prescription; and providing, by the server to one or more of the dental office and the dental laboratory, authorization to proceed with the dental restoration if the one or more identifiers match the authorized identifiers and/or if the data associated with the one or more identifiers matches the data contained in the corresponding prescription.

In an embodiment, the server determines a maximum yield related to the frame of material and a number of units of the maximum yield remaining Authorization to proceed with the dental restoration is further based on at least one unit of the maximum yield remaining.

In an embodiment, providing authorization to proceed comprises the server instructing a mill located at the dental office or the dental laboratory to construct the dental restoration. If the one or more identifiers do not match the authorized identifiers and/or if the data associated with the one or more identifiers does not match the data contained in the corresponding prescription, the server prevents a mill located at the dental office or the dental laboratory from constructing the dental restoration.

According to an additional embodiment, the server prepares a record file comprising information from the dental office and the dental laboratory relating to the dental restoration; the server compares parameters of the record file to validation criteria stored in a database accessible by the server; and the server provides, to one or more of the dental office and the dental laboratory, an authorization certification indicating approval of the dental restoration if the parameters of the record file match the validation criteria.

In an embodiment, the record file comprises one or more of: dentist identifier, case identifier, patient identifier, tooth number, type of restoration, scan file, design file, scanner model, CAD software, material parameters utilized in CAD, material type, and mill model. The validation criteria comprise one or more of: validated scanner models, validated material parameters, validated material types, and validated mill models.

According to an embodiment, the server stores the authorization certification and associates the authorization certification with one or more of the dental office, the dental laboratory, and a patient for whom the dental restoration is intended.

In another embodiment, the server associates the one or more identifiers with identification information of the one or more of the dental office and the dental laboratory, and maintains a record of the identification information with data relating to the dental restoration.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

Embodiments of the present invention relate to the incorporation of authentication and security aspects into systems and processes for fabricating dental restorations. According to embodiments, a scanner is used in a dental office to take a scan of a patient's mouth, a file of which is sent to a laboratory, such as a dental laboratory. The dental laboratory designs the dental restoration with specialized design software taking into account the scan of the mouth as well as a prescription from the dental office. Parameters defining the designed dental restoration are contained in a design file. The design file is used to create milling specifications defining instructions for milling the designed dental restoration. The materials for the dental restoration are loaded into a mill, located at the dental office, where the dental restoration is fabricated in accordance with the milling specifications. This procedure allows for a same-day patient visit in which the patient is examined and fitted with the dental restoration.

The term "same-day patient visit" means a patient treatment period of one calendar day. In some embodiments, the patient may be permitted to leave the dentist's office and return that same day. In other embodiments, the same-day patient visit may be a single office visit.

The terms "single office visit", "one office visit" or similar means a single block of contiguous time. Because of the relatively short periods involved, the patient need not leave the dentist's office and in some instances not even leave the examination room. In some embodiments, a single office visit may be about 3 hours or less, or about 2.5 hours or less, about 2 hours or less, about 1.5 hours or less, or less than 1 hour, or any range between two of these values.

The term "dental office" as used herein means the patient's dentist's office. It is intended to mean the normal everyday working office of the doctor.

The term "dental laboratory" as used herein means a professional dental laboratory separate and distinct from a dental office. A dental laboratory is an off-site facility for development and/or production of dental restorations. For clarity, the dental laboratory does not install the restorative devices, and does not perform the traditional functions of a dental office.

Figure 1:
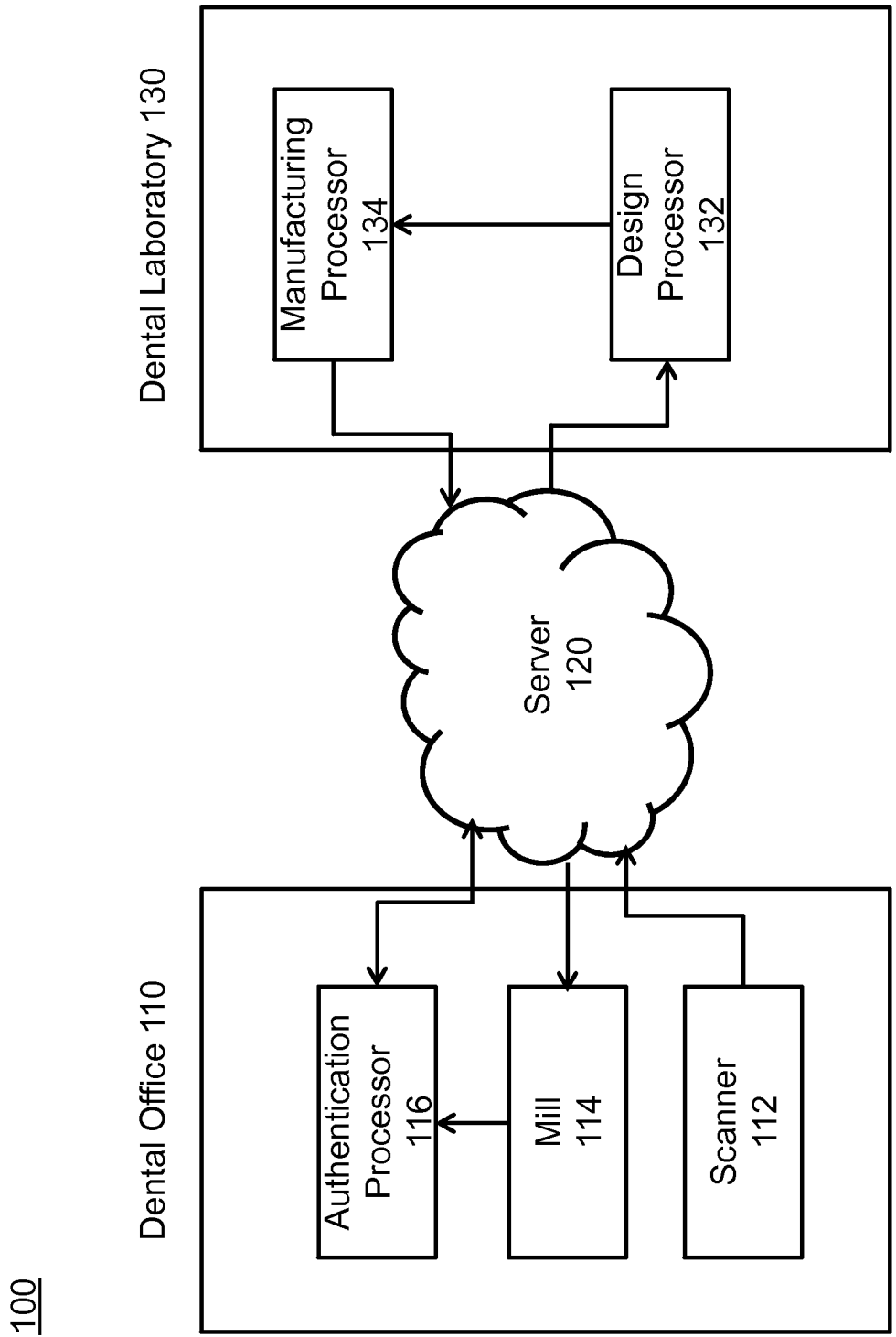
FIG. 1 is a block diagram representing a system for fabricating dental restorations, according to an embodiment.

FIG. 1 provides a block diagram illustration of a system 100 for fabricating dental restorations, according to an embodiment. The system 100 includes a dental office 110, a server 120, and a dental laboratory 130.

Features of the dental office 110 include a scanner 112, a mill 114, and an authentication processor 116. The scanner 112, such as an intra-oral scanner (IOS) or other scanner available in the dental industry, is used to scan a patient, and, in particular, a prepared tooth of a patient. A dentist or other professional working at the dental office 110 prepares the tooth to be fitted with a fabricated dental restoration. The dental restoration needs to be designed for the patient and to meet certain requirements specified by the dentist.

The mill 114 is capable of milling (i.e., cutting and forming) the dental restoration. According to an embodiment, the mill 114 is a computer numerical control (CNC) mill. The use of a CNC mill allows for an automated system in which computer-aided design (CAD) and computer-aided manufacturing (CAM) programs are used to create files that provide commands for the operation of the CNC mill.

The authentication processor 116 is configured to process information associated with the authenticity of the fabricated dental restoration, as described in greater detail below.

The system 100 for fabricating dental restorations also includes a server 120 and a dental laboratory 130. The server 120 is configured to facilitate communication between the dental office 110 and the dental laboratory 130. The server 120 may be one or more dedicated servers for a particular entity or entities, or the server 120 may be one or more servers that are part of a cloud-based server. The server 120 may be part of a communication network. Examples of communication networks include, for example, a local area network (LAN), a wide area network (WAN), and the computers and networks forming the Internet. The server 120 performs various verification, security, and authentication processes before transmitting data to and/or between the dental office 110 and the dental laboratory 130. The verification processes serve to ensure that the dental office 110 and the dental laboratory 130 are authorized to communicate with one another and to ensure that the data to be transmitted is valid and meets certain requirements. Moreover, the security processes serve to ensure that authorized materials are used for the dental fabrications, while the authentication processes serve to verify that authorized processes are used in the fabrication. Further details related to the functionality of the server 120 are provided below.

The dental laboratory 130 is responsible for designing the dental restoration, taking into account the scan of the mouth as well as a prescription from the dental office 110. In the embodiment shown in FIG. 1, the dental laboratory 130 includes a design processor 132 and a manufacturing processor 134. The design processor 132 may comprise CAD software for designing the dental restoration. The manufacturing processor 134 may comprise CAM software for formulating the specifications to be used by the mill 114 for milling the dental restoration (i.e., the milling specifications).

In the embodiment illustrated in FIG. 1, the mill 114 located at the dental office 110 mills the dental restoration, while the dental laboratory 130 is remotely providing the technology for the design of the dental restoration. In some embodiments, the dental laboratory 130 may place the mill 114 in the dental office 110 based on a contractual relationship between the dental office 110 and the dental laboratory 130. In this embodiment, the dental office 110 does not have to invest in the design technology but still achieves a same-day patient visit, which may be one-hour or less in duration.

In this embodiment, the mill 114 functions in a similar manner as a remote printer, in that it does not require any kind of design software (e.g., CAD) in the dentist office 110. In fact, there is little hands-on intervention in the dentist office other than placing a restorative material in the mill 114. The dental laboratory 130 remotely controls the mill 114, minimizing or eliminating the need for any kind of intervention on the dentist side in the design and fabrication of the dental restoration.

In other embodiments, a separate mill may also be provided at the dental laboratory 130.

Figure 2:
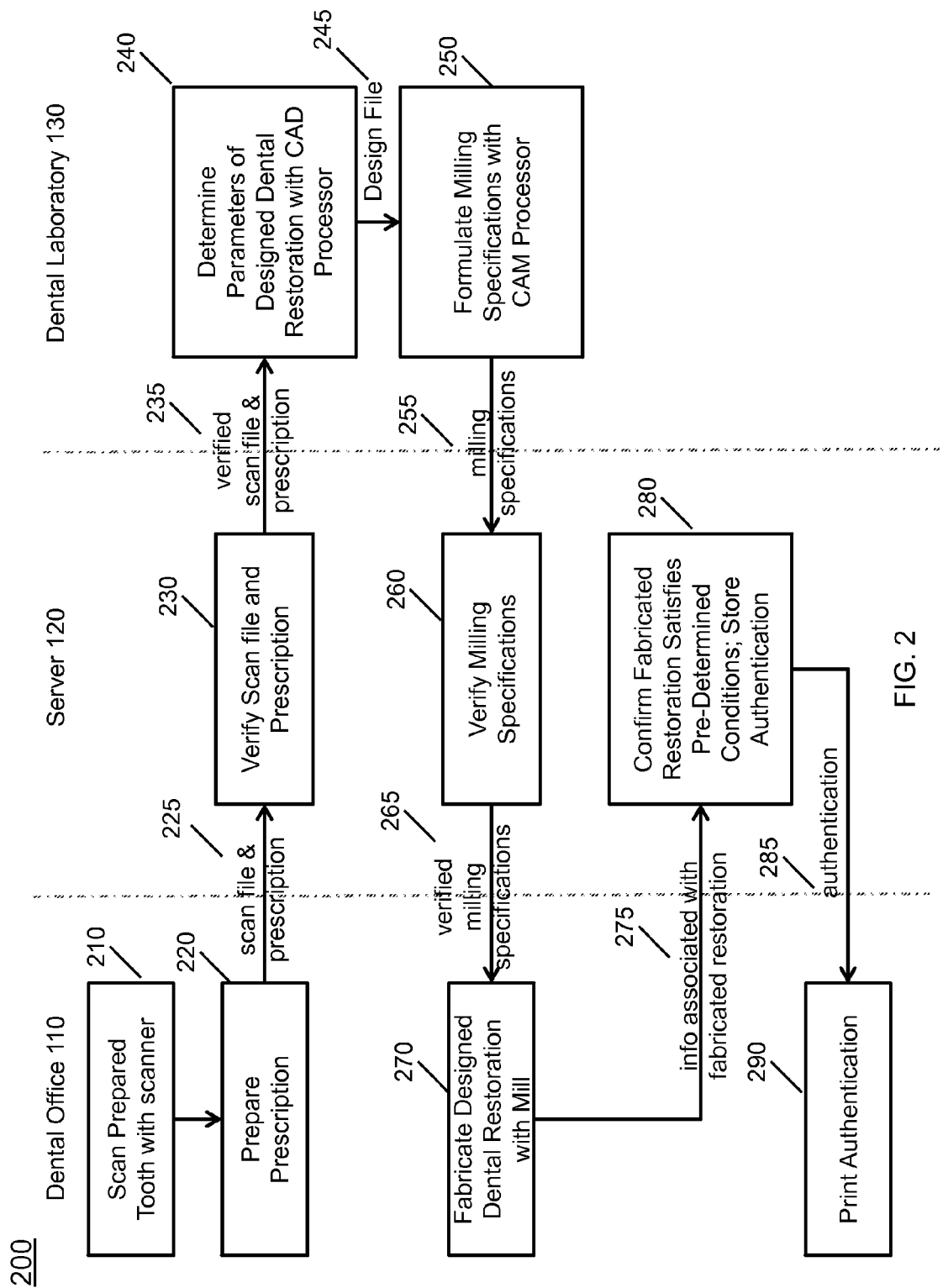
FIG. 2 is a flowchart illustrating a method of fabricating dental restorations, according to an embodiment.

FIG. 2 provides a data flow representation 200 of a method of fabricating dental restorations, according to an embodiment. The data flow begins at the dental office 110 with, at 210, a prepared tooth being scanned with the scanner 112 to create a scan file containing a three-dimensional image. At 220, a prescription is prepared, the prescription being associated with the scan file. The prescription may include details related to the dental restoration to be designed and fabricated, such as, but not limited to, a tooth number; a type of dental restoration, such as, for example, inlay, onlay, crown, and bridge; a restorative material, such as, for example, ceramic, Nano-resin, zirconia, and composite materials; a shade for the designed dental restoration, such as, for example, Vita A1-D4; and a manufacturer and/or brand name. The prescription may also include information related to the patient, such as, but not limited to, a patient name, patient demographic information, and patient medical information. Other instructional or identifying information may be included with the prescription.

At 225, the scan file and the prescription are sent from the dental office 110. At 230, the server 120 verifies the scan file and the prescription. At 235, the verified scan file and prescription are sent to the dental laboratory 130. Details relating to the verification of the scan file and the prescription are provided in greater detail below.

At 240, the design processor 132 at the dental laboratory 130 determines the design characteristics for a dental restoration associated with the scan file. The design characteristics may be in the form of a design file defining parameters of the designed dental restoration and may be created by CAD software running on the design processor 132. In particular, a trained dental laboratory technician uses the CAD software to examine and manipulate the three-dimensional image in the scan file to define the characteristics and physical parameters of the designed dental restoration. The designed dental restoration is designed to sufficiently meet the functional and aesthetic needs of the patient, which are defined in the prescription.

At 245, the design file is transmitted from the design processor 132 to the manufacturing processor 134, also at the dental laboratory 130. At 250, the manufacturing processor 134 formulates the milling specifications that define instructions for milling the designed dental restoration. As noted above, CAM software may be running on the manufacturing processor 134. The CAM software defines how the mill 114 will mill the designed dental restoration from a material provided in the mill 114. The mill 114 utilizes a series of tools or burs to shape a dental material into the designed dental restoration, and the CAM software may be programmed, according to an embodiment, to define the following mill specifications: (i) cutting tools or burs utilized by the mill 114 and their positions within the mill 114; (ii) a three-dimensional geometry of the material to be milled; and (iii) tool and tool path strategies to achieve the designed dental restoration.

At 255, the milling specifications are sent from the dental laboratory 130. At 260, the server 120 verifies the milling specifications, and, at 265, transmits the verified milling specifications to the dental office 110. Verification of the milling specifications may generally relate to ensuring the specifications adhere to the prescription. Details relating to the verification of the milling specifications are provided in greater detail below.

At 270, the mill 114 located at the dental office 110, fabricates the designed dental restoration in accordance with the milling specifications.

When the verified milling specifications are provided to the dental office 110, the dental office 110 may be alerted that the mill 114 is ready to begin a fabrication. This may be done through a processor or controller associated with the mill 114. For example, a message may be retrieved or a signal activated, indicating the prescription associated with the fabrication and the restorative material to be used. An operator at the dental office 110 loads and secures the restorative material into the mill 114, and then the fabrication may be initiated.

When the fabrication is completed, the mill 114 may provide a signal indicating completion, at which point the fabricated designed dental restoration is unloaded from the mill 114, and an operator, such as the dentist, performs minor finishing procedures to the fabricated designed dental restoration to prepare for seating in the patient's mouth.

In some embodiments, a security step involving material authentication can be incorporated into the process. An optional authentication relating to the process and parameters used to create the fabricated designed dental restoration may also be done. With further reference to FIG. 2, at 275, information associated with the fabricated designed dental restoration is sent from the authentication processor 116, in communication with the mill 114, at the dental office 110 to the server 120. The information may include, but is not limited to, the restorative material, the manufacturer and/or brand of the restorative material, and the milling strategy as outlined in the milling specifications. At 280, the server 120 uses this information as well as the scan file, the prescription, and the design file to determine if requirements and standards are satisfied. At 285, if the server 120 determines that the requirements and standards are satisfied, an authentication message is sent to the authentication processor 116. At 290, the authentication processor 116 may print an authentication, such as a label or other identifier, through an associated printer. Additionally or alternatively, the requirements and standards, including the authentication of the requirements and standards, may be stored in a database or table accessible by the server 120 and may be established to indicate that the fabricated designed dental restoration is sufficient as defined by the requirements and standards. The security process and additional details related to the authentication process are further described below with respect to FIG. 5.

In some embodiments, prior to fabricating the designed dental restoration at 270, the dental office 110 may provide data associated with the restorative material to the server 120 to verify that the correct material (i.e., the prescribed material) is being used. In some embodiments, if the server 120 identifies that the correct material is not being used, the server 120 may prevent the mill 114 from milling the dental restoration. If the correct material is being used, the fabrication and subsequent authentication steps may be implemented as described above. Additional details related to this security step are described below with reference to FIG. 5.

The verification of the data, i.e., the scan file and prescription at 230 and the milling specifications at 260, by the server 120 may include the server 120 confirming the authenticity of the scan file, the prescription, and the milling specifications, as well as confirming a pre-existing relationship between the dental office 110 and the dental laboratory 130. In confirming the authenticity of the scan file, the prescription, and the milling specifications, the server 120 may verify certain features, such as, but not limited to: the dental office 110 being a valid participant, the dental laboratory 130 being a valid participant, the scan file containing sufficient information for creating a design file and/or the milling specifications, the prescription containing sufficient information for creating the design file and/or the milling specifications, and the milling specifications being complete. In the verification of the data, the server 120 may access stored information, such as valid participants and requirements for the scan file, the design file, and the milling specifications; the server may also store the scan file, the design file, and/or the milling specifications at an accessible memory device (not shown).

Figure 3:
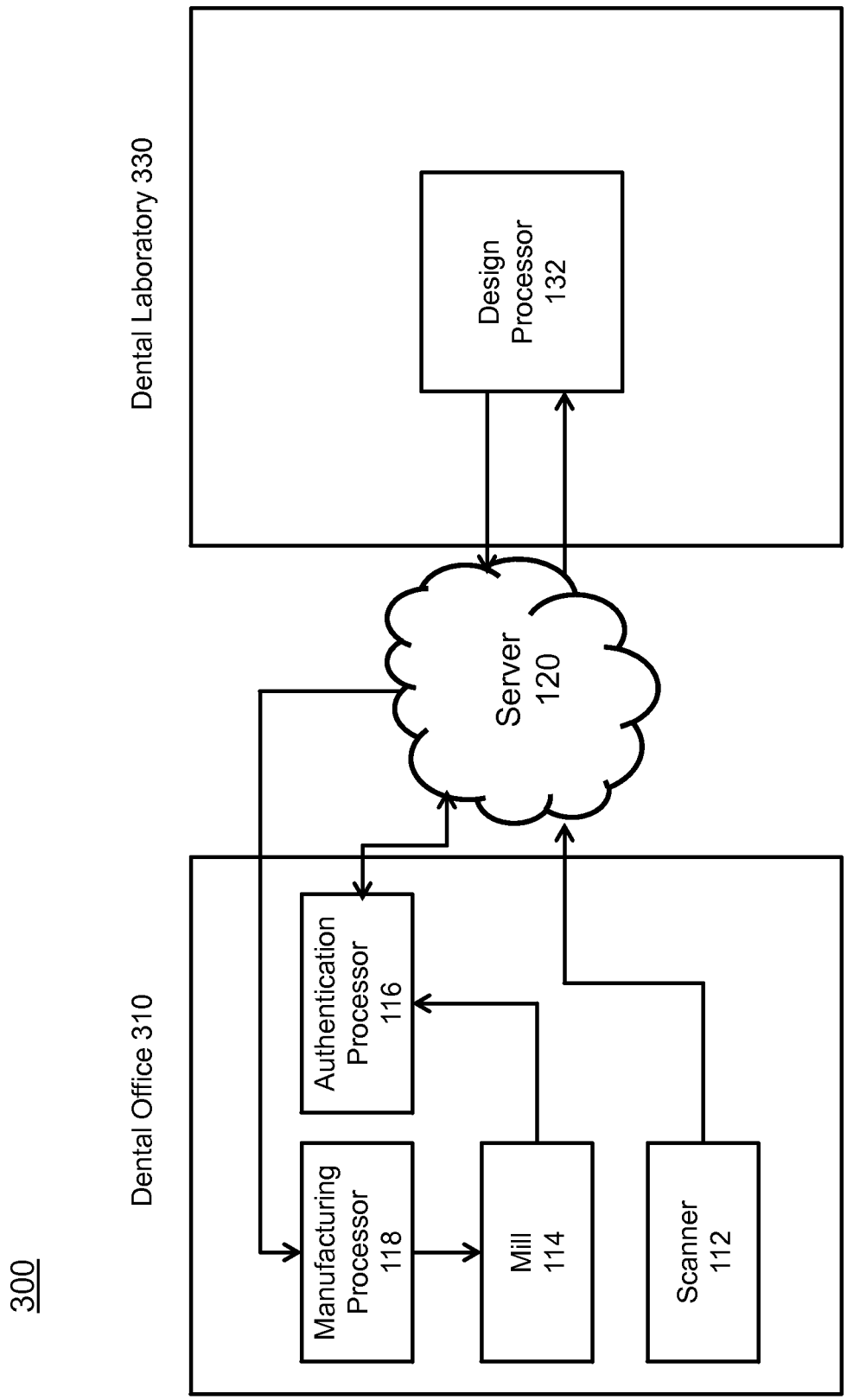
FIG. 3 is a block diagram representing a system for fabricating dental restorations, according to an additional embodiment.

FIG. 3 provides a block diagram illustration of a system 300 for fabricating dental restorations, according to an additional embodiment. The system 300 includes a dental office 310, the server 120, and a dental laboratory 330. The main differences between the systems 100 and 300 are the location of the manufacturing processor that runs, according to an embodiment, the CAM software for formulating the milling specifications based on the design file. In the embodiment shown in FIG. 3, the dental office 310, in addition to including the scanner 112, the mill 114, and the authentication processor 116, includes the manufacturing processor 118. In this embodiment, the dental laboratory 330 still includes the design processor 132 for creating the design file based on the scan file and the prescription. The dental laboratory 330 transmits the design file, via the server 120, to the dental office 310 for the formulation of the milling specifications via the manufacturing processor 118.

Figure 4:
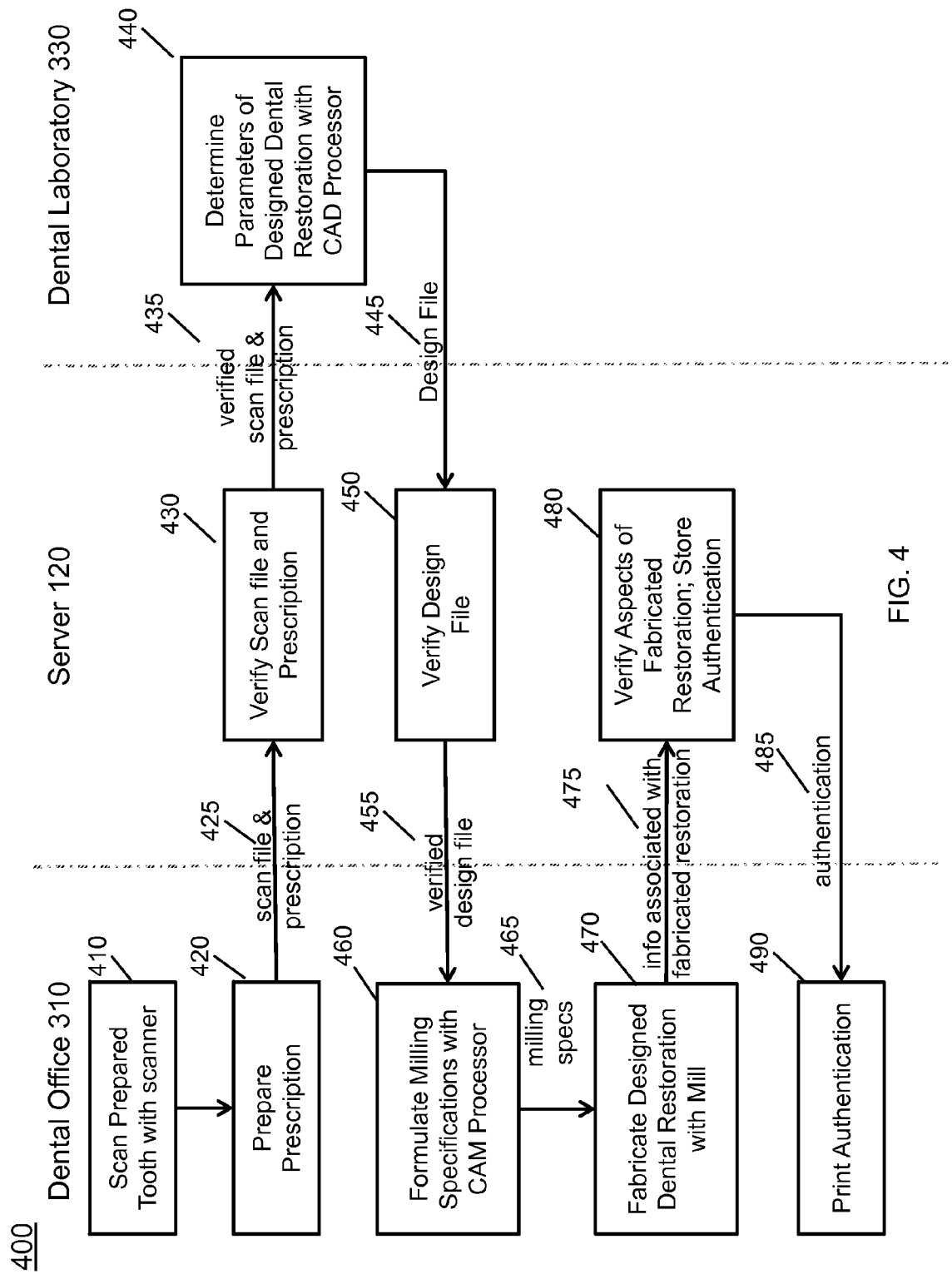
FIG. 4 is a flowchart illustrating a method of fabricating dental restorations, according to an additional embodiment.

FIG. 4 provides a data flow representation 400 of a method of fabricating dental restorations, according to an embodiment. At 410, a prepared tooth is scanned with the scanner 112 in the dental office 310 to create a scan file containing a three-dimensional image. At 420, a prescription is prepared, the prescription associated with the scan file.

At 425, the scan file and the prescription are sent from the dental office 110. At 430, the server 120 verifies the scan file and the prescription. At 435, the verified scan file and prescription are sent to the dental laboratory 330.

At 440, the design processor 132 at the dental laboratory 330 determines the design characteristics for a dental restoration associated with the scan file. The design characteristics may be in the form of a design file defining parameters of the designed dental restoration and may be created by CAD software running on the design processor 132.

At 445, the design file is transmitted from the design processor 132. At 450, the server 120 verifies the design file, and, at 455, transmits the verified design file to the dental office 310.

At 460, the manufacturing processor 118 at the dental office 310 formulates the milling specifications that define instructions for milling the designed dental restoration. At 465, the milling specifications are provided to the mill 114 for fabrication of the dental restoration. At 470, the mill 114 located at the dental office 310, fabricates the designed dental restoration in accordance with the milling specifications.

At 475, information associated with the fabricated designed dental restoration is sent from the authentication processor 116, in communication with the mill 114, at the dental office 310 to the server 120. At 480, the server 120 uses this information as well as the scan file, the prescription, and the design file to determine if the requirements and standards are satisfied. At 485, if the server 120 determines that the requirements and standards are satisfied, an authentication message is sent to the authentication processor 116. At 490, the authentication processor 116 prints an authentication, such as a label or other identifier. In addition to or alternative to printing an authentication label or identifier, the server 120 may store an indication of the authentication in a database or table accessible by the server 120. The indication of the authentication may be established to indicate that the fabricated designed dental restoration is sufficient as defined by the requirements and standards. Moreover, the authentication may be associated with a patient-specific and/or a dental office account. In this manner, a record may be created and linked to the patient and/or the dental office 310 to indicate the various dental restorations associated with the patient and/or the dental office 310.

According to embodiments, a security process is used to verify the use of authorized materials in the dental mill, and an authentication process verifies that an authorized process and prescribed materials are used to create the dental restoration.

According to an embodiment, each frame containing restoration material has an identifier, e.g., a barcode that provides information such as, but not limited to, manufacturer or brand, material type, size, shape, color, shade, etc., with respect to the blank to be milled. Other technical information may be associated with the identifier depending upon the material. The identifiers are stored in a database in or accessible to the server 120. Each identifier may be assigned a maximum yield in units based on the type and size of the material contained in the frame. Each time a restoration is ready to be fabricated, prior to milling, a dental office or dental laboratory personnel scans the identifier, which is sent to the server 120. The server 120 verifies if the identifier exists in the database, serving as an indication that the material is authorized for use. The server 120 may also verify if the scanned identifier matches that indicated in the milling instructions or the dentist prescription. In the event the identifier does not exist or does not match that required by the milling instructions, an audible, visual or other alert is issued at the dental office 110, 310 to alert personnel that the material is not authorized or that the materials do not match those prescribed by the dentist (e.g., incorrect brand or manufacturer or incorrect material). In some embodiments, the mill 114 may be prevented from working on a non-authorized material. In some embodiments, the dental office or laboratory personnel may be permitted to override the alarm and prepare the restoration from an alternative material. With respect to the maximum yield, the server 120 confirms that the maximum yield has not yet been met for a particular identifier. If the maximum yield is not met, the server 120 verifies the material and subtracts a unit from the maximum yield. In this manner, the maximum yield check adds an extra layer of security by prohibiting subsequent use of the frame by the dental office 110, 310 or dental laboratory 130, 330 adding material to a frame whose original material has been exhausted.

According to an additional embodiment, a further security check may be incorporated by adding a shipment code to a plurality of frames, with the shipment code identifying the customer (i.e., the dental office 110, 310 or the dental laboratory 130, 330) and the plurality of frames that make up a shipment/order/package. The various shipment codes are stored in database in or accessible to the server 120. In addition to scanning the frame identifier, the dental office 110, 310 or the dental laboratory 130, 330 may scan or enter the shipment code. The server 120 verifies if the shipment code matches a code stored in the database, if the shipment code is associated with the dental office 110, 310 or the dental laboratory 130, 330 transmitting the shipment code, and if the shipment code is associated with the frame identifier also being scanned. In this manner, the shipment code serves as an extra confirmation that a valid user is utilizing the frame and material for a dental restoration.

According to an additional embodiment, a dental office 110, 310 or a dental laboratory 130, 330 may purchase materials with a license to use a predetermined number of units of the material. An account may be created and stored relating to this arrangement. The material does not have a frame identifier but may still be authorized by the server 120 confirming that an account is established and that the predetermined number of units has not been exhausted.

According to yet another embodiment, identification information, such as geographic information, may be associated with the purchaser (e.g., the dental office 110, 310) of restoration materials. The identification information of the purchaser may be linked to the identifier, e.g., the barcode, of the material. When the identifier is scanned and sent to the server 120 during the fabrication process, the server 120 maintains a record of the identification information linked to the particular material being used. In this manner, records of the users of the material are linked to the actual material, which may be of interest to the manufacturer or sales associates. For example, if the identification information is, as one example, a zip code of the dental office 110, 310 using the restoration material, the server 120 will compile a listing of zip codes that used materials by a certain manufacturer. The server 120 may provide this information to various entities, such as manufacturers, sales associates, etc. Moreover, the identification information is not limited to geographic information (e.g., zip code, area code, city, state, etc.) but may also include the type of facility (e.g., university or private practice) or the size of the facility (based on, for example, the number of patients seen during a given time period or the number of practitioners).

Figure 5:
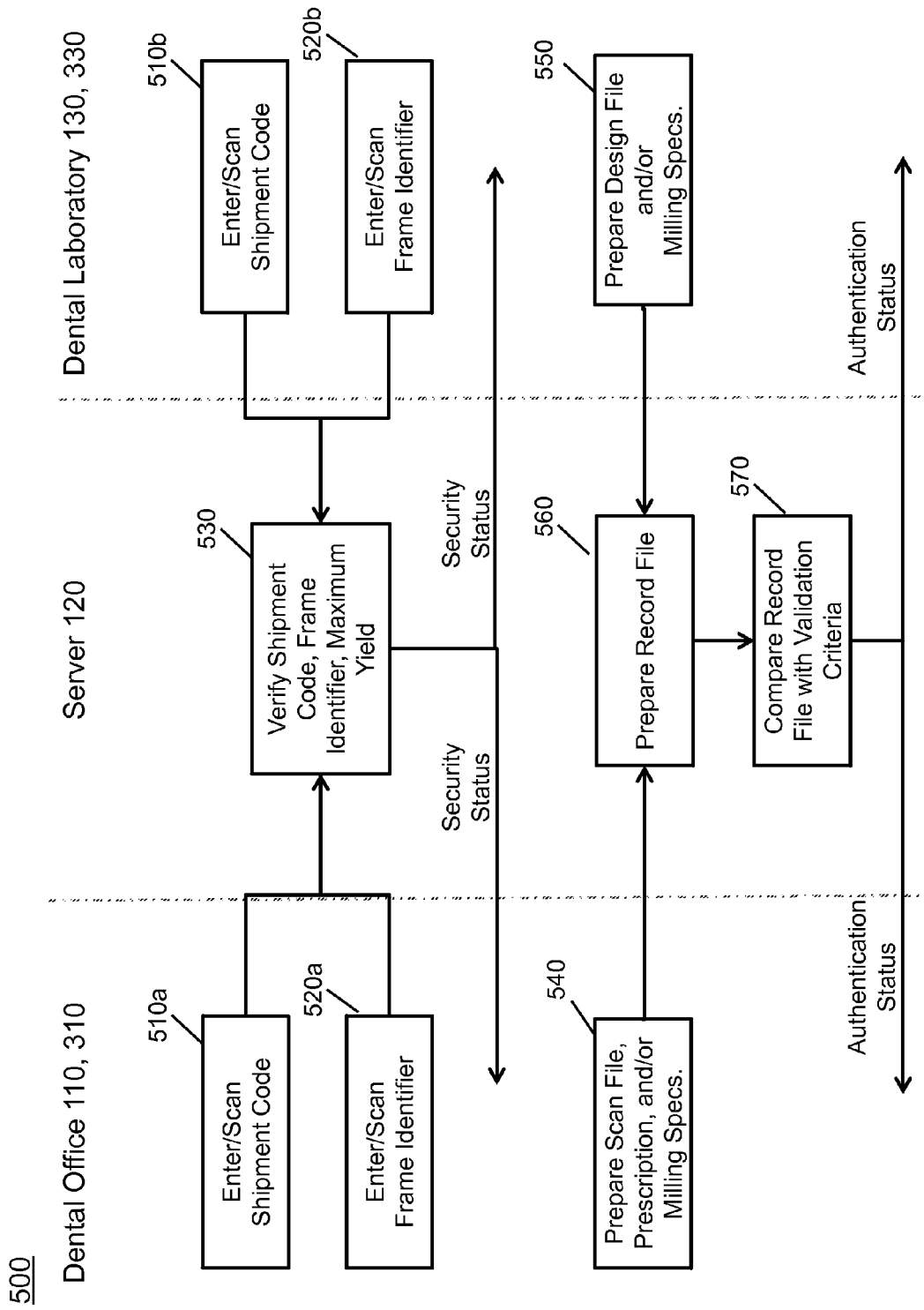
FIG. 5 is a flowchart illustrating a method of verifying security and authentication in the fabrication of a dental restoration, according to an embodiment.

FIG. 5 provides a data flow representation 500 of a method of verifying security and authentication in the fabrication of dental restorations, according to an embodiment. The method shown in FIG. 5 may incorporate the features shown in FIGS. 2 and 4 and may serve as additional add-on features. At 510*a*, a shipment code is entered or scanned at the dental office 110, 310. At 520*a*, a frame identifier is entered or scanned at the dental office 110, 310. Alternatively, at 510*b*, a shipment code is entered or scanned, and at 520*b*, a frame identifier is entered or scanned at the dental laboratory 130, 330. This entered/scanned information is sent to the server 120, where, at 530, a security check is done to determine if the shipment code, frame identifier, and maximum yield associated with the frame identifier are secure. The server 120 sends a security status to the dental office 110, 310 or to the dental laboratory 130, 330 indicating if the material is authorized based on the analyzed information.

During the processes described above with respect to FIGS. 1-4, various information is provided to the server 120 from the dental office 110, 310 and the dental laboratory 130, 330. For example, at 540, the scan file, prescription, and/or the milling instructions are provided from the dental office 110, 310 to the server 120. At 550, the design file and the milling specifications are provided from the dental laboratory 130, 330 to the server 120. These pieces of information are not typically sent at one time, but are instead sent and processed during the dental fabrication process as described above with respect to FIGS. 2 and 4.

At 560, the server 120 uses the received information to create a record file. The record file may include one or more of: dentist identifier, case identifier, patient identifier, tooth number, type of restoration, manufacturer and/or brand of restoration material, scan file, design file, scanner model, CAD software, material parameters utilized in CAD, material type, and mill model. Other relevant information may also be included.

At 570, the record file is compared against validation criteria stored in a database accessible to the server 120. The validation criteria may be established to determine if the designed dental restoration meets certain pre-approved criteria. The validation criteria may also include information from the dentist prescription to ensure the prescription is being adhered to (e.g., the type of material, the manufacturer, etc.). The validation criteria may include, but is not limited to, one or more of: validated scanner models, validated material parameters, validated material types, validated manufacturer and/or brand, and validated mill models. Based on the comparison, the dental restoration process is either authenticated or denied, and this status is sent to the dental office 110, 310 and/or the dental laboratory 130, 330. The status may also be stored and saved with the record file to be later accessed as part of a patient or office record. In some embodiments, as described above, an invalidated material and/or process may result in the mill 114 being prevented from milling the dental restoration.

According to embodiments provided herein, while a scanner 112 is used in a dental office 110, 310 to take a scan of a patient's mouth, the design of the dental restoration is done offsite at a dental laboratory 130, 330. The dental laboratory 130 formulates the milling specifications and defines instructions for milling the designed dental restoration. The milling specifications are formulated based on the scan received by the dental laboratory. In one embodiment, those milling specifications are used to define milling instructions at the dental lab 130 and which are transmitted to the mill 114 at the dental office which receives remote instructions for formulating the designed dental restorations. In another embodiment, the milling instructions may be developed by dental laboratory personnel on the CAM software resident at the dental office 310, in which case the mill 114 communicates with the manufacturing processor 118 within the dental office 310. This procedure allows for a same-day patient visit in which the patient is examined and fitted with the dental restoration. In other embodiments relating to security and authentication aspects, the dental laboratory 130 may also include a mill. Generally, the CAM software performs the two functions: 1) formulating the milling specifications, and 2) defining instructions for the milling machine. These two functions may reside together in a single CAM software, or separately. When separate, is possible that the formulating functionality may reside in the dental laboratory, while the defining instructions functionality may reside in the dental office. In either case, the dental laboratory will control the operation of both functions of this software directly or remotely. In this manner, the dental laboratory, and not the dental office, controls the formulation of the milling specifications as well as the milling instructions.

The processors 116, 118, 132, and 134 may be a processing device, computing device, or the like for performing calculations and operations described herein. As used herein, a controller or a processor should be understood to include any number of controllers or processors. While the controller and processors described herein have been broken down as individual controllers and processors performing certain tasks, this is done for illustrative purposes. Embodiments of the present invention can include single or multiple controller or processors performing the roles described. Furthermore, the roles described as separate controllers or processors herein can, in some embodiments, be performed by separate or common controllers or processors or any subset therein. The server 120 includes one or more processors for performing the calculations and operations described herein.

The processors 116, 188, 132, and 134 and the server 120 may interface with one another, and may also interface with one or more memory devices, such as read only memory (ROM), random access memory (RAM), and one or more optional non-transitory memory devices such as, for example, an external or internal DVD drive, a CD ROM drive, a hard drive, flash memory, a USB drive, or the like. The memory devices may be configured to include individual files and/or one or more databases for storing any software modules, instructions, or data.

Program instructions, software, or interactive modules for performing any of the functional steps associated with the processes as described above may be stored in the ROM and/or the RAM. Optionally, the program instructions may be stored on a tangible computer readable medium such as a compact disk, a digital disk, flash memory, a memory card, a USB drive, an optical disc storage medium, such as a Blu-ray™ disc, and/or other recording medium.

An optional display interface may permit information from the processors 116, 188, 132, and 134 and the server 120 to be displayed on a display in audio, visual, graphic, and/or alphanumeric format. For example, a display may be associated with the mill 114 to indicate to an operator details and instructions related to the fabrication of the designed dental restoration. Communication with external devices may occur using various communication ports that may be attached to one or more communications networks, such as the Internet or a local area network, or directly to a portable computing device such as a notebook computer. An interface may allow for receipt of data from input devices such as a keyboard, a mouse, a joystick, a touch screen, a remote control, a pointing device, a video input device, an audio input device, and the like. Communications within the system or any part thereof or to external devices or systems can be achieved through any suitable arrangement, including but not limited to wired or wireless communications or combinations thereof.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A method of fabricating dental restorations, the method comprising:
　facilitating, by a server, communication between a dental office and a dental laboratory, the communication comprising:
　　transmitting by the dental office to the dental laboratory a scan file comprising a scan of a patient, wherein the scan file is generated by a scanner located in the dental office;
　　verifying, by the server, the scan file transmitted by the dental office;
　　receiving by the dental laboratory the scan file;
　　transmitting by the dental laboratory to the dental office design characteristics for a designed dental restoration associated with the scan file, wherein the design characteristics comprise at least one of (i) a design file defining parameters of the designed dental restoration and (ii) milling specifications defining instructions for milling the designed dental restoration;

verifying, by the server, the design characteristics transmitted by the dental laboratory;

receiving by the dental office the design characteristics, wherein a mill located at the dental office fabricates the designed dental restoration in accordance with the design characteristics; and verifying, by the server, the fabricated designed dental restoration;

wherein each of the verifying steps are related to verifying authenticity and authorized relationships.

2. The method of claim 1, wherein the design characteristics received by the dental office comprise at least one of: (i) the design file defining parameters of the designed dental restoration, wherein a computer-aided manufacturing (CAM) processor at the dental office formulates the milling specifications from the design file and provides the milling specifications to the mill for fabrication of the designed dental restoration; and (ii) the milling specifications defining instructions for milling the designed dental restoration, wherein a computer-aided manufacturing (CAM) processor at the dental laboratory formulates the milling specifications from the design file and provides the milling specifications to the mill at the dental office for fabrication of the designed dental restoration.

3. The method of claim 2, wherein the design file defining parameters of the designed dental restoration is created by a computer-aided design (CAD) processor at the dental laboratory based upon the scan file and a prescription provided by the dental office.

4. The method of claim 3, wherein the prescription provided by the dental office comprises one or more of: (i) a tooth number; (ii) a type of dental restoration; (iii) a restorative material; (iv) a shade for the designed dental restoration; and (v) a manufacturer.

5. The method of claim 1, wherein verifying the scan file comprises confirming, by the server, at least one of: (i) authenticity of the scan file; (ii) authenticity of a prescription associated with the scan file; and (iii) a pre-existing relationship between the dental office and the dental laboratory; and wherein verifying the design characteristics comprises confirming, by the server, at least one of: (i) authenticity of the design characteristics; and (ii) a pre-existing relationship between the dental laboratory and the dental office.

6. The method of claim 1, wherein verifying, by the server, the fabricated designed dental restoration, comprises:

receiving, at the server from the dental office, information associated with the fabricated designed dental restoration;

confirming, by the server, that that fabricated designed dental restoration satisfies pre-determined conditions;

transmitting, by the server, an authentication of the fabricated designed dental restoration to the dental office; and printing, by an authentication processor at the dental office, an authentication indication associated with the fabricated designed dental restoration.

7. A system for fabricating dental restorations, the system comprising:

a server configured to facilitate communication between a dental office and a dental laboratory, the communication comprising:

a scan file transmitted by the dental office to the dental laboratory, the scan file comprising a scan of a patient, wherein the scan file is generated by a scanner located in the dental office;

design characteristics transmitted by the dental laboratory to the dental office, the design characteristics for a designed dental restoration associated with the scan file, wherein the design characteristics comprise at least one of (i) a design file defining parameters of the designed dental restoration and (ii) milling specifications defining instructions for milling the designed dental restoration;

wherein a mill located at the dental office fabricates the designed dental restoration in accordance with the design characteristics;

wherein the server is further configured to facilitate authentication between the dental office and the dental laboratory, comprising:

verifying the scan file transmitted by the dental office;

verifying the design characteristics transmitted by the dental laboratory; and verifying the fabricated designed dental restoration;

wherein each of the verifying steps are related to verifying authenticity and authorized relationships.

8. The system of claim 7, wherein the design characteristics received by the dental office comprise at least one of (i) the design file defining parameters of the designed dental restoration, wherein a computer-aided manufacturing (CAM) processor at the dental office formulates the milling specifications from the design file and provides the milling specifications to the mill for fabrication of the designed dental restoration; and (ii) the milling specifications defining instructions for milling the designed dental restoration, wherein a computer-aided manufacturing (CAM) processor at the dental laboratory formulates the milling specifications from the design file and provides the milling specifications to the mill at the dental office for fabrication of the designed dental restoration.

9. The system of claim 8, wherein the design file defining parameters of the designed dental restoration is created by a computer-aided design (CAD) processor at the dental laboratory based upon the scan file and a prescription provided by the dental office.

10. The system of claim 9, wherein the prescription provided by the dental office comprises one or more of: (i) a tooth number; (ii) a type of dental restoration; (iii) a restorative material; (iv) a shade for the designed dental restoration; and (v) a manufacturer.

11. The system of claim 7, wherein verifying the scan file comprises the server confirming at least one of: (i) authenticity of the scan file; (ii) authenticity of a prescription associated with the scan file; and (iii) a pre-existing relationship between the dental office and the dental laboratory; and wherein verifying the design characteristics comprises the server confirming at least one of: (i) authenticity of the design characteristics; and (ii) a pre-existing relationship between the dental laboratory and the dental office.

12. The system of claim 7, wherein verifying the fabricated dental restoration comprises:

receiving, at the server from the dental office, information associated with the fabricated designed dental restoration;

confirming, by the server, that that fabricated designed dental restoration satisfies pre-determined conditions;

transmitting, by the server, an authentication of the fabricated designed dental restoration to the dental office; and printing, by an authentication processor at the dental office, an authentication indication associated with the fabricated designed dental restoration.

13. A method of verifying aspects relating to a dental restoration, the method comprising:

receiving, by a server coupled to a dental office and to a dental laboratory, one or more identifiers from one or more of the dental office and the dental laboratory, the one or more identifiers respectively relating to a frame of material for the dental restoration and a package of a plurality of frames;

comparing, by the server, the one or more identifiers to authorized identifiers stored in a database accessible by the server;

comparing, by the server, data associated with the one or more identifiers to data contained in a corresponding prescription; and providing, by the server to one or more of the dental office and the dental laboratory, authorization to proceed with the dental restoration if at least one of (i) the one or more identifiers match the authorized identifiers and (ii) the data associated with the one or more identifiers matches the data contained in the corresponding prescription.

14. The method of claim 13, further comprising:

determining, by the server, a maximum yield related to the frame of material and a number of units remaining of the maximum yield;

wherein authorization to proceed with the dental restoration is further based on at least one unit remaining of the maximum yield.

15. The method of claim 13, wherein providing authorization to proceed comprises the server instructing a mill located at the dental office or at the dental laboratory to construct the dental restoration.

16. The method of claim 13, further comprising:

if at least one of (i) the one or more identifiers do not match the authorized identifiers and (ii) the data associated with the one or more identifiers does not match the data contained in the corresponding prescription, preventing, by the server, a mill located at the dental office or at the dental laboratory from constructing the dental restoration.

17. The method of claim 13, further comprising:

preparing, by the server, a record file comprising information from the dental office and the dental laboratory relating to the dental restoration;

comparing, by the server, parameters of the record file to validation criteria stored in a database accessible by the server;

providing, by the server to one or more of the dental office and the dental laboratory, an authorization certification indicating approval of the dental restoration if the parameters of the record file match the validation criteria;

storing, by the server, the authorization certification; and associating the authorization certification with one or more of the dental office, the dental laboratory, and a patient for whom the dental restoration is intended.

18. The method of claim 17, wherein the record file comprises one or more of: dentist identifier, case identifier, patient identifier, tooth number, type of restoration, scan file, design file, scanner model, CAD software, material parameters utilized in CAD, material type, and mill model; and wherein the validation criteria comprise one or more of: validated scanner models, validated material parameters, validated material types, and validated mill models.

19. The method of claim 13, further comprising:

associating, by the server, the one or more identifiers with identification information of the one or more of the dental office and the dental laboratory; and maintaining a record, by the server, of the identification information with data relating to the dental restoration.

* * * * *